United States Patent [19]

Ingram et al.

[11] Patent Number: 5,169,569

[45] Date of Patent: Dec. 8, 1992

[54] METHOD OF MAKING A ONE-PIECE INTRAOCULAR LENS

[76] Inventors: Richard Ingram, 7681 Dartmoor Ave., Goleta, Calif. 93117; John Lynch, P.O. Box 721, Santa Paula, Calif. 93061-0721; Jerry Wilson, 5630 Messina, Goleta, Calif. 93117

[21] Appl. No.: 740,517

[22] Filed: Aug. 5, 1991

[51] Int. Cl.[5] .............................................. B29D 11/00
[52] U.S. Cl. ..................................... 264/2.7; 264/1.7; 264/160; 264/291; 264/547; 264/572
[58] Field of Search .................. 264/1.1, 1.4, 1.7, 2.7, 264/544, 547, 572, 573, 160, 291

[56] References Cited

U.S. PATENT DOCUMENTS 3,140,325  7/1964  Graff ................................. 264/544
4,961,746  10/1990  Lim et al. ............................ 264/1.7

FOREIGN PATENT DOCUMENTS 2640591  3/1978  Fed. Rep. of Germany ...... 264/544
40516  4/1981  Japan ................................. 264/544
2134838  8/1984  United Kingdom ............... 264/544

Primary Examiner—James Lowe
Attorney, Agent, or Firm—Charles C. Logan, II

[57] ABSTRACT

The PMMA (Polymethyl methacrylate) plastic used to produce one-piece intraocular lenses is modified by a novel thermoplastic pressure forming process to produce a much tougher material with improved mechanical properties. The improved material exhibits greater ductility and fatigue resistance than conventional cast PMMA sheet, resulting in a one-piece lens that is less prone to breakage from implantation or use.

5 Claims, 5 Drawing Sheets

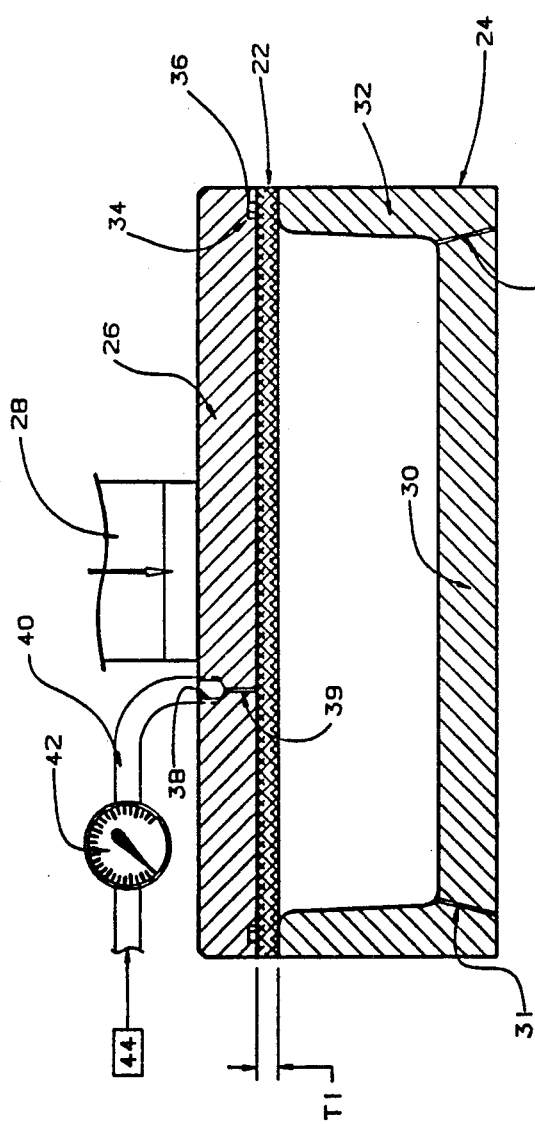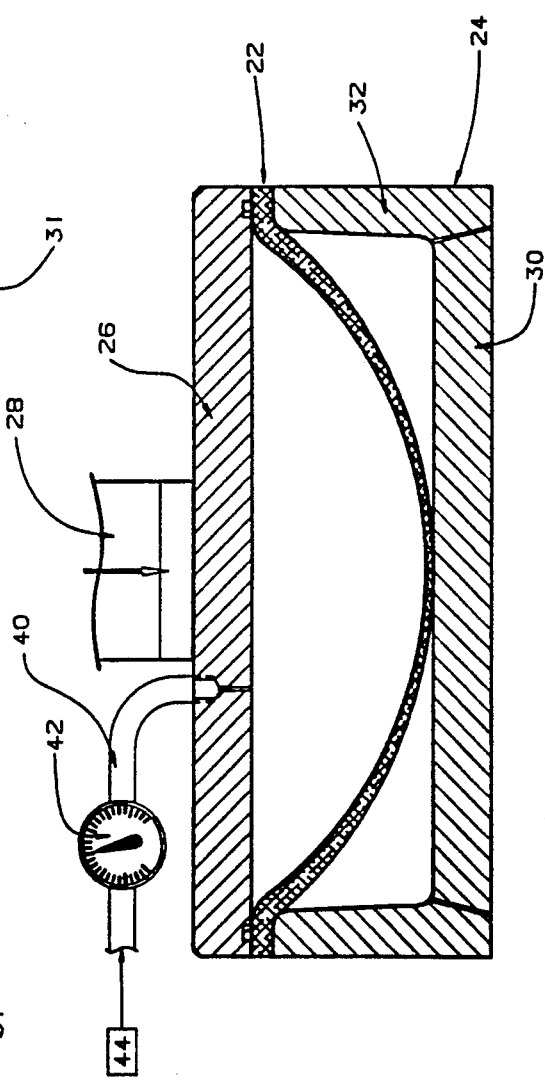

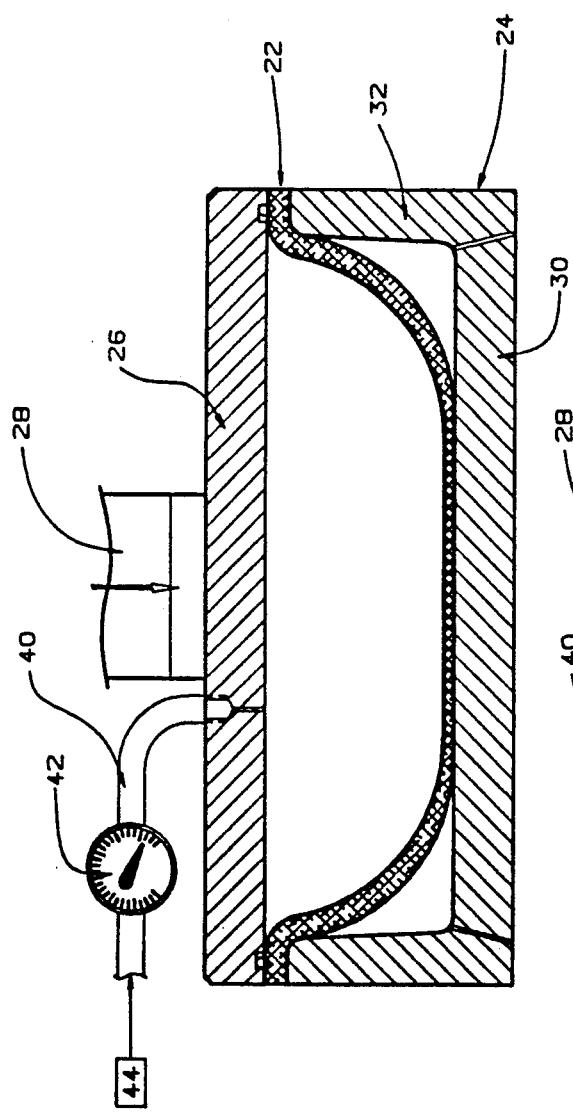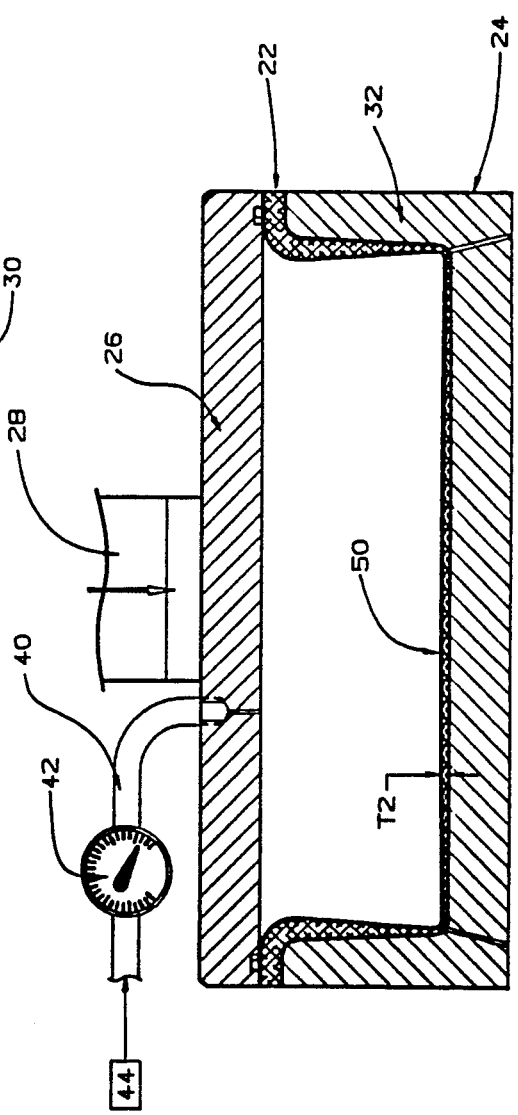

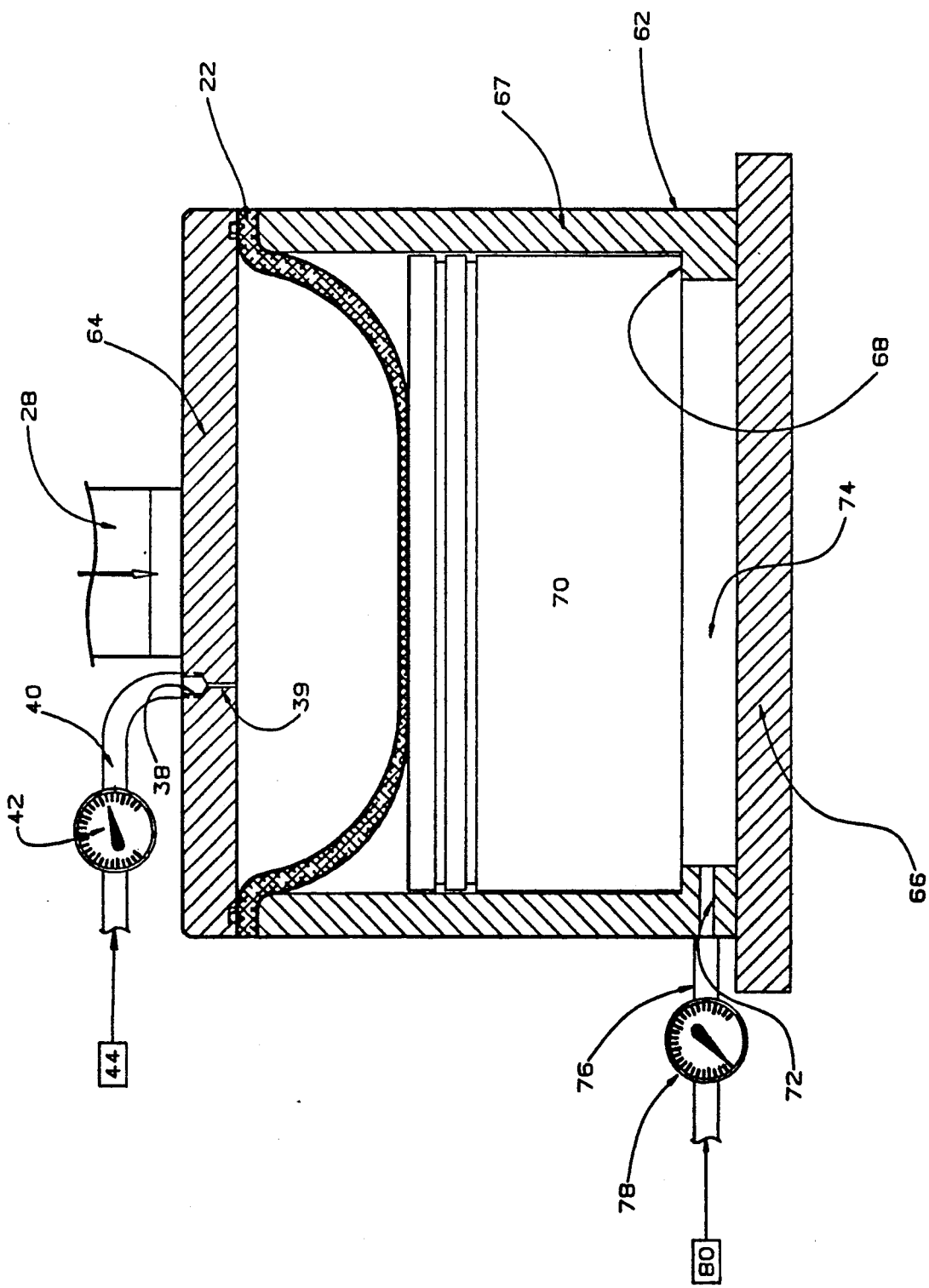

METHOD OF MAKING A ONE-PIECE INTRAOCULAR LENS

BACKGROUND OF THE INVENTION

The invention relates to intraocular lenses and more specifically to a new process for improving the ductility and fatigue resistance of the PMMA (polymethyl methacrylate) that is machined to form one-piece lenses.

Intraocular lenses are small plastic lenses that are inserted into the interior of the eye after the cataractous natural lens has been removed. The concept of the modern intraocular lens was introduced shortly after the Second World War by the English cataract surgeon and inventor Harold Ridley. His observations of eye trauma in British pilots caused by plastic canopy shrapnel revealed that the acrylic plastic material caused few complications such as infection or foreign body rejection. He concluded that acrylic might make a good material for an artifical lens, and it has in fact proved to be very biocompatible in the eye for long periods.

Modern intraocular lenses have been made by several methods, most notably lathe turning and injection or compression molding. Initially, the optic was made as a separate piece from the haptics, which are flexible supporting structures that act as a centering spring to located the lens within the eye. The haptic filaments in this type of lens (three-piece construction) are made from a monofilament of either PMMA or Polypropylene suture material, which is heat formed to the desired shape. The haptics are attached to the lens by inserting them in a microscopic hole in the lens edge and heat staking them in place. Lenses made this way have proven excellent in service with good flexation characteristics.

More recently, with the advent of very accurate computer controlled machinery, it has become practical to machine the entire lens from one piece of plastic material. This is usually done with a combination of lathe turning operations combined with very precise milling of the profiles necessary to produce the lens shape. Among the advantages of one-piece construction over the earlier three-piece methods (separate optic/haptics) are: fewer pieces, therefore lower labor and fabrication costs, also less concern arout the strength of connections between components, and the one-piece design has fewer places for possible entrapment of pyrogenic materials on the lens.

The material most commonly used for one-piece IOL (intraocular lens) construction is cast PMMA sheet. It is commonly known as "acrylic" plastic, and is characterized by good optical clarity and rigid mechanical properties. Some of its advantages over the other optical materials are its proven compatibility as an ocular implant material, good optical properties including UV light absorption, and mechanical rigidity which makes possible the machining of highly polished and accurate optical surfaces.

The one-piece lens manufacturing method also has some disadvantages. The size of an IOL is quite small, with optic diameters typically 5 to 7 millimeters in diameter, and overall diameter of the haptic structure about 12 to 15 millimeters. The width and thickness of the haptic filaments is about 0.17 millimeters (0.0065 inches ), and consequently these structures are very delicate and fragile. Further, since the PMMA material from which they are machined is a cast polymer, it has isotropic mechanical properties (generally the same strength in any direction). Just as a cast piece of metal is weaker than a metal extrusion or forging, the one-piece lens haptics are weaker than haptics used on three-piece lenses, which are much tougher since they are made from a drawn filament material which is very tough and flexible.

The haptics are most susceptible to weakening and breakage during the implantation proceedure when the surgeon must deflect the loops considerably to insert the lens into the eye. Even after a lens is implanted, the haptics must continue to bear a certain amount of stress exerted within the eye from muscles and outside forces (i.e. rubbing the eye). It is therefore very desirable to have a material with flexibility, toughness, and fracture resistance to make a more durable one-piece lens.

Several inventions relating to contact lenses and intraocular lenses have been granted U.S. patents. The Wichterle U.S. Pat. No. 3,361,858 is directed to a method for reshaping a xerogel by mechanical removal and swelling to form a hydrogel contact lens. The Shepherd U.S. Pat. No. 4,208,364 is directed to a process for producing contact lenses. The Haardt et al U.S. Pat. No. 4,407,776 is directed to a mold and proceedure for producing truncated contact lenses. The Hwang U.S. Pat. No. 4,786,444 is directed to a method and apparatus for making optical devices such as intraocular lenses. The Akhavi U.S. Pat. No. 4,847,020 is directed to a process of molding an optic for an intraocular lens.

SUMMARY OF THE INVENTION

The invention consists of a process and apparatus which heats and stretches cast PMMA sheet plastic for the purpose of improving the mechanical characteristics of the material. This strengthened material is then used in the manufacture of one-piece intraocular lenses or other opthamalic implant devices that have thin or delicate sections which are subject to bending stresses. During forming the material is pulled in all directions in a uniform manner by means of blowing the sheet into a hemispherical bubble and thence sent into a mold which forms a flattened circular portion. It is desirable that the finished product be a flat sheet, as that is the form required for normal one-piece intraocular manufacturing. It is also important that the mechanical characteristics of the modified material be uniform and consistant across the sheet and without regard for orientation, e.g. having no "grain" direction. In the process described here, the uniformity of the material is achieved by two elements, the first being that a circularly shaped mold is used which causes the stretching action to occur in all directions. Secondly, the mold proportions are designed to produce a flat stretched sheet which has minimum thickness variation from center to edge.

During the forming process, as the bubble is being created by air pressure, the material is thinnest in the center and progressively thicker toward the periphery. Once the center of the bubble contacts the bottom of the mold and begins to flatten, additional stretching occurs around the edges which eventually makes the edge of the sheet thinner than the center. It is desirable that the thickness variation of the flat portion of the sheet is minimized by proper design of the fixture.

In a second embodiment of the invention, an improved fixture is used which employs a movable piston acting as the "floor" of the mold. During the forming process, as the bubble of stretched material is being forced down onto the floor of the mold, the piston is simultaneously advanced upwards against the formed part, thereby causing a reduction in the stretching action on the periphery of the molded piece. By tailoring the timing and motion of the piston during the forming cycle, it is possible to achieve more uniform thickness of the flat portion of the stretched material.

The improvement in mechanical properties that the novel process produces includes an increase in flexural strength, decrease in flexural modulus (stiffness), and an increase in ductility and fatigue resistance. These results were substantiated by an independent materials testing laboratory.

BRIEF DESCRIPTION OF THE DRAWINGS

FIG. 3 is a schematic cross sectional view of the mold used in method #1 during step one of its use;

FIG. 4 is a schematic cross sectional view of the mold used in method #1 during step two of its use;

FIG. 5 is a schematic cross sectional view of the mold used in method #1 during step three of its use;

FIG. 6 is a schematic cross sectional view of the mold used in method #1 during step four of its use;

FIG. 7 is a schematic cross sectional view illustrating an alternative mold that is used with method #2 and it is shown in the step after the sheet has initially been placed between the top and bottom portions of the mold;

DESCRIPTION OF THE PREFERRED EMBODIMENT

Figure 1:
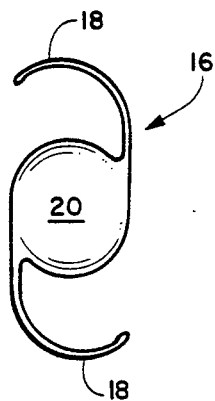
FIG. 1 is a top plan view of a one-piece intraocular lens.
Figure 2:
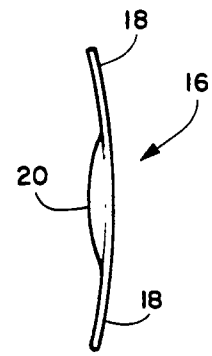
FIG. 2 is a side elevation sectional view of the intraocular lens of FIG. 1.
Figure 9:
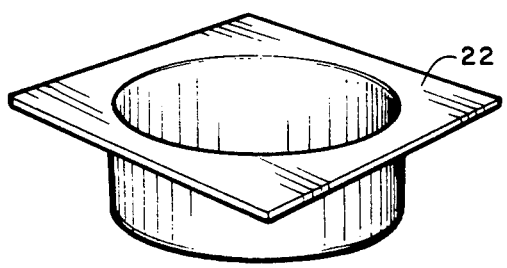
FIG. 9 is a front perspective view showing the sheet of PMMA after it has been formed in either of the molds of method #1 and method #2.

The novel improved one-piece intraocular lens and method of making the same will now be described by referring to FIGS. 1-12 of the drawings. An example of a finished one-piece intraocular lens 16 is illustrated in FIGS. 1 and 2. It has a pair of haptics 18 integrally connected to the lens portion 20.

The first method for making the improved one-piece intraocular lens and the mold used with this process is illustrated in FIGS. 3-6. A cast sheet 22 of PMMA material would have been previously heated in a circulating air oven to a temperature of 175 degrees C. for 45 minutes to bring the entire sheet to the forming condition. Sheet 22 would then quickly be placed over mold base 24 and the mold lid 26 would then be lowered and clamped with sufficient hydraulic mechanical pressure by a ram 28 to counteract the force which will be exerted by the air pressure during forming in the mold. A typical mold base 24 would be, but is not limited to, a diameter of 11.5 inches and a depth of 2.75 inches. In this example, mold base 24 has a bottom wall 30 and a cylindrical side wall 32. Mold lid 26 has an annular groove 34 in its bottom surface that receives an O-ring seal 36 that seals the edges of sheet 22 between the top and bottom halves of the mold. Pressure port 38 with a restriction 39 is formed in mold lid 26. Hose 40 having an air gauge 42 has its one end connected to pressure port 38 and its opposite end connected to a source of pressurized air 44.

In FIG. 4, pressurized air is applied through orifice 39 forcing sheet 22 down into a hemispherical configuration. The orifice 39 limits the flow rate to prevent rupturing the sheet by forming too rapidly. As the air pressure is applied, the pliable sheet is forced into the mold, and is stretched until it firmly contacts the mold sides and base. Typically the air pressure in the above example is about 100 psi to insure a sufficiently flat part (circular portion 50).

Figure 10:
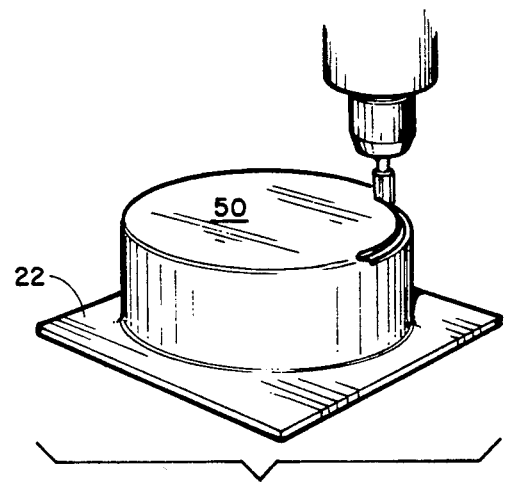
FIG. 10 is a front perspective view illustrating the manner in which the circular portion is cut free from the structure illustrated in FIG. 9.
Figure 11:
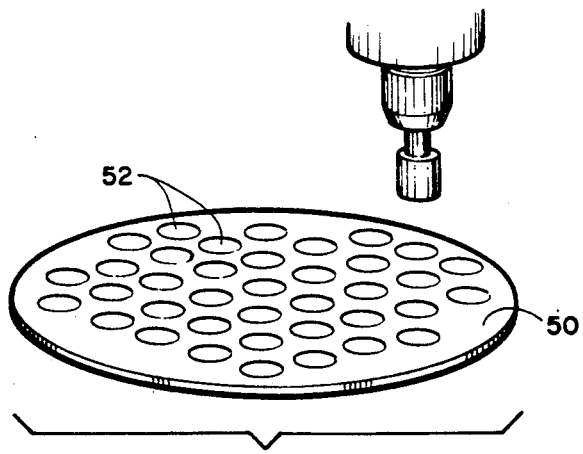
FIG. 11 is a front perspective view illustrating the manner in which small disks are cut from the circular portion.
Figure 12:
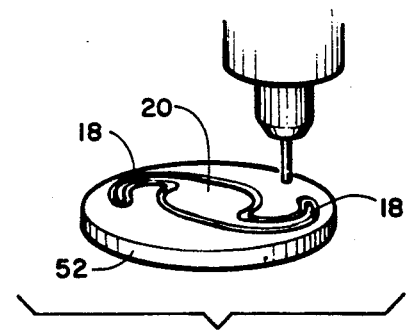
FIG. 12 is a perspective view illustrating the manner in which the one-piece intraocular lens is milled from one of the disk.

Sheet 22 is cooled in mold 24 until it is below the softening point and then removed from the mold for air cooling to room temperature. Sheet 22 then has the configuration illustrated in FIG. 9. In FIG. 10, it has been turned over and placed on a mill where the circular portion 50 is cut free. The next step in the operation is illustrated in FIG. 11 where a plurality of small disks 52 are cut from circular portion 50. These disks 52 are turned and milled (see FIG. 12) into the lenses 16 illustrated in FIGS. 1 and 2.

The initial thickness of sheet 22 is Tl. The final sheet thickness should be from 0.25 Tl to 0.75 Tl to achieve the desired mechanical properties. The size of material that can be processed by this method is not limited to the examples above, and in fact could be expanded in principal to very large thick sheets. An advantage of this system is that the equipment needed is simple, with few moving parts and most of the work being done by pneumatic or hydraulic power.

Figure 8:
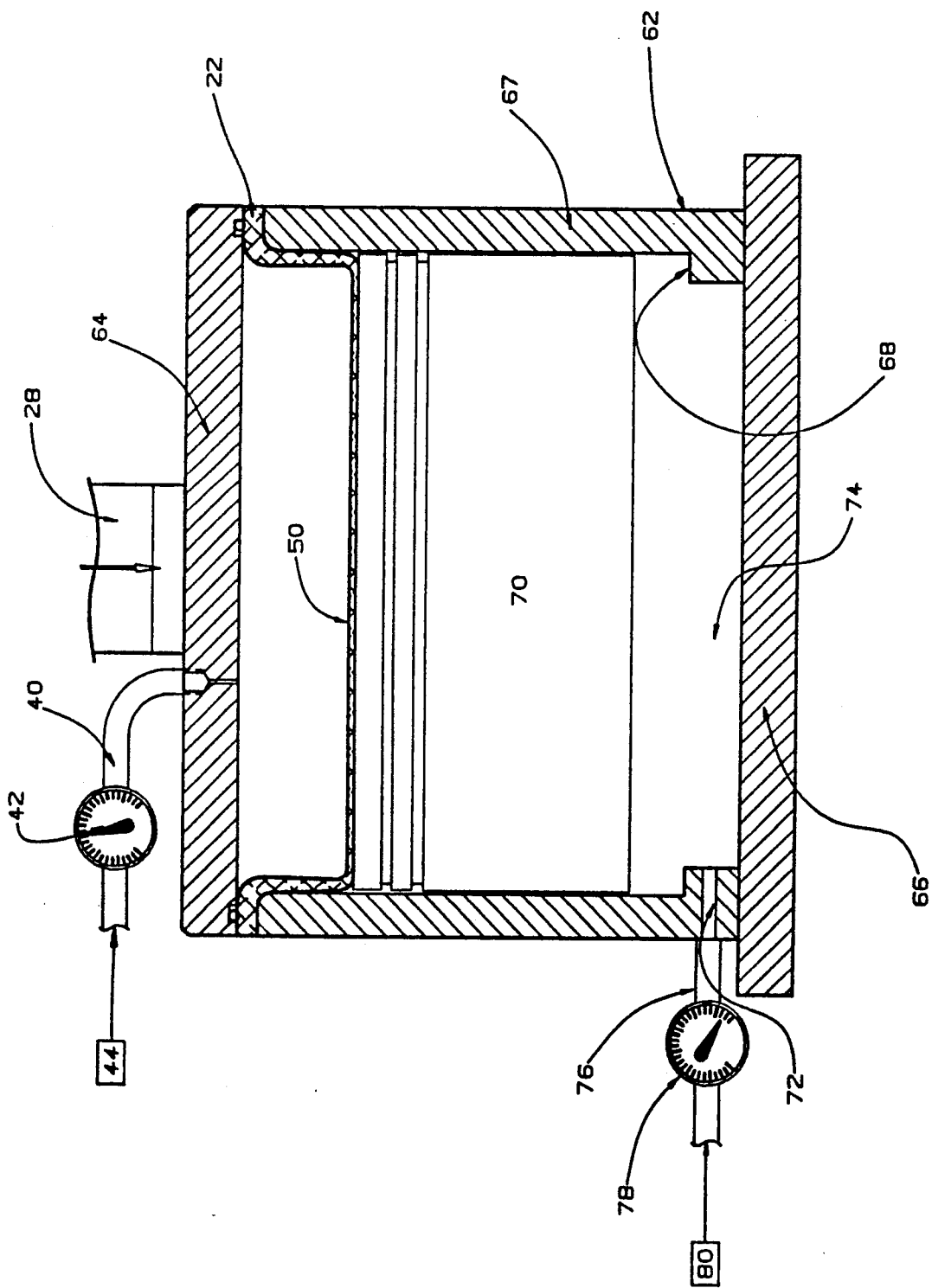
FIG. 8 is a schematic illustration similar to that of FIG. 7 but showing the next method #2.

The second method for stretching sheet 22 is illustrated in FIGS. 7 and 8. These Figures show a mold base 62 having a mold lid 64. Mold base 62 has a bottom wall 66 and cylindrical side walls 67 having an annular bottom stop 68 adjacent its bottom inside surface. A piston 70 is mounted therein and normally rests on bottom stop 68. A pressure port 72 passes through side wall 67 and is in communication with air chamber 74 and hose 76. An air gauge 78 is mounted in line with hose 76 which is also connected to a source of air pressure 80. In FIG. 7, heated sheet 22 is formed down in contact with piston 70, but not fully stretched (piston supported on bottom stops 68). In FIG. 8, higher pressure is applied to the bottom of piston 70, driving it up and flattening the sheet without additional stretching. The steps following this would be the same as those illustrated in FIGS. 9-12 in order to produce the one-piece occular lens 16.

What is claimed is:

1. A method for producing an improved one-piece intraocular lens from a cast sheet of PMMA (polymethyl methacrylate) plastic comprising the following steps:
   a) heating a cast sheet of PMMA in an oven to a predetermined temperature for a predetermined amount of time to bring the entire sheet to a forming condition;
   b) placing the cast sheet of PMMA in a mold having a lid and a mold base, said lid having a bottom surface, said mold base having cylindrical side walls that extend upwardly from the top surface of a bottom wall, said cylindrical side walls having a top surface and also an inner wall surface, the peripheral edges of the sheet being captured between the bottom surface of the mold lid and the top surface of the cylindrical side walls of the mold base;

c) inserting pressurized air at a predetermined initial pressure through the mold lid thereby stretching and forming the sheet of PMMA into a hemispherical bubble configuration;

d) continuing to admit pressurized air through the mold lid thereby causing further stretching of the sheet of PMMA causing it to be pressed against the inner wall surface of the cylindrical side walls and the top surface of the bottom wall of the mold base, a circular portion of substantially uniform thickness PMMA is formed against the top surface of the bottom wall;

e) allowing the sheet to cool in the mold a predetermined amount of time;

f) removing the stretched sheet of PMMA from the mold;

g) removing said circular portion from the remainder of said stretched sheet of PMMA;

h) cutting a plurality of small disks from said circular portion; and i) turning and milling said disks into intraocular lenses having integrally formed haptics.

2. The method recited in claim 1 wherein the pressure of the air inserted into said mold in step (d) is greater than the pressure of the air inserted into the mold in step (c).

3. The method recited in claim 1 wherein the thickness of said cast sheet of PMMA in step (a) is T1 and the thickness of said stretched circular portion in step (d) is in the range between 0.75 T1–0.25T1.

4. The method recited in claim 1 wherein the pressurized air in step (c) passes through a pressurized port in the mold lid and it has restriction means to prevent rupturing the sheet of PMMA by two rapid inflation.

5. A method of producing an improved one-piece ocular lens from a cast sheet of PMMA (polymethyl methacrylate) plastic comprising the following steps:

a) heating a cast sheet of PMMA in an oven to a predetermined temperature for a predetermined amount of time to bring the entire sheet to a forming condition;

b) placing the cast sheet of PMMA in a mold having a lid and a mold base, said lid having a bottom surface, said mold base having cylindrical side walls that extend upwardly from the top surface of a bottom wall, said cylindrical side walls having a top surface and also an inner wall surface, the peripheral edges of the sheet being captured between the bottom surface of the mold lid and the top surface of the cylindrical side walls of the mold base;

c) inserting pressurized air at a predetermined initial pressure through the mold lid thereby stretching and forming the sheet of PMMA into a hemispherical bubble configuration;

d) inserting pressurized air at a higher predetermined pressure than in step (c) into the base of the mold below a piston mounted therein thereby driving it upwardly and flattening the sheet without additional stretching, a circular portion of the substantially uniform thickness PMMA is formed against the top wall of said piston;

e) allowing the sheet to cool in the mold a predetermined amount of time;

f) removing the stretched sheet of PMMA from the mold;

g) removing said circular portion from the remainder of said stretched sheet of PMMA;

h) cutting a plurality of small disks from said circular portions; and i) turning and milling said disks into intraocular lenses having integrally formed haptics.

* * * * *